: US005677473A

United States Patent [19]

Tomifuji et al.

[11] Patent Number: 5,677,473
[45] Date of Patent: Oct. 14, 1997

[54] PROCESS FOR THE PREPARATION OF BRANCHED CHAIN FATTY ACIDS AND ALKYL ESTERS THEREOF

[75] Inventors: Takeshi Tomifuji; Hiroshi Abe; Yoshihisa Matsumura; Yasumitsu Sakuma, all of Wakayama, Japan

[73] Assignee: Kao Corporation, Tokyo, Japan

[21] Appl. No.: 443,158

[22] Filed: May 17, 1995

[30] Foreign Application Priority Data

May 18, 1994 [JP] Japan .................... 6-129589

[51] Int. Cl.$^6$ .................. C07C 51/00; C07C 51/353
[52] U.S. Cl. ............. 554/158; 554/125; 554/141; 554/145; 502/77; 502/78
[58] Field of Search ................ 554/158, 125, 554/141, 145; 502/77, 78

[56] References Cited

U.S. PATENT DOCUMENTS

| 4,371,469 | 2/1983 | Foglia et al. .................. 260/405.6 |
| 4,943,546 | 7/1990 | Travers et al. . | |

FOREIGN PATENT DOCUMENTS

| 0 206 143 | 12/1986 | European Pat. Off. . |
| 0 523 838 | 1/1993 | European Pat. Off. . |
| 523838 | 1/1993 | European Pat. Off. . |
| 2 696 450 | 4/1994 | France . |
| 2 696 451 | 4/1994 | France . |
| 1 211 158 | 2/1966 | Germany . |
| 1 228923 | 9/1989 | Japan . |

OTHER PUBLICATIONS

J.C.S., pp. 2158–2163, 1948, R.M. Barres, "Synthesis and Reactions of Mordenite".
Shokubai Koza, vol. 10, pp. 84–87, 1986 (with partial English translation).

Primary Examiner—Jose' G. Dees
Assistant Examiner—Deborah D. Carr
Attorney, Agent, or Firm—Oblon, Spivak, McClelland, Maier & Neustadt, P.C.

[57] ABSTRACT

A process for preparing branched chain fatty acids or alkyl esters thereof comprising at least a step wherein unsaturated fatty acids having 10 to 25 carbon atoms, alkyl esters thereof or mixtures thereof are subjected to skeletal isomerization reaction in the presence of water or a lower alcohol at a temperature of 150° to 350° C. using a zeolite as a catalyst, the zeolite having a linear pore structure of pore size that is small enough to retard dimerization and large enough to allow diffusion of the branched chain fatty acids or alkyl esters thereof.

10 Claims, No Drawings

PROCESS FOR THE PREPARATION OF BRANCHED CHAIN FATTY ACIDS AND ALKYL ESTERS THEREOF

BACKGROUND OF THE INVENTION

1. Field of the Invention

The present invention relates to a process for the preparation of long-chain fatty acids having branched alkyl chains, or alkyl esters thereof (hereinafter also referred to as "branched chain fatty acids, etc."), which are important starting materials for the synthesis of cosmetic bases, fiber treating agents, hair treating agents, lubricating oil additives, etc.

2. Discussion of the Related Arts

Branched chain fatty acids have usually been obtained as by-products in the production of dimerized fatty acids or esters(hereinafter referred to as "dimer acids"). There have been only a few attempts to produce branched chain fatty acids, etc. as the main product.

Specifically, dimer acids are produced by thermally polymerizing fatty acids or esters having unsaturated bonds in the presence of various acidic catalysts. During this production, a part of the starting fatty acids or esters shows skeletal isomerization, resulting in the formation of branched chain fatty acids as by-products. The branched chain fatty acids, etc. are separated from dimer acids by distillation, or other means, hydrogenated and then separated from linear alkyl fatty acids or esters by solvent fractionation, etc.

It is difficult to analyze the structure of the branched chain fatty acids, etc. in detail. They are generally mixtures of a large number of isomers which have some branched alkyl chains having 1 to 4 carbon atoms at different branching positions in the principal alkyl chain. For example, when the starting unsaturated fatty acid is oleic acid or linolic acid derived from beef tallow, soybean oil, toll oil, or the like, the resulting branched fatty acids are called isostearic acid. Isostearic acid has a feature of a low solidifying point (titer, below 10° C.) although it is a saturated fatty acid.

However, there have been no attempts to improve the above process except for those to improve the yield of the main desired products of dimer acids. Already disclosed methods include the use of crystalline clay minerals and water as catalysts of the process (U.S. Pat. No. 2,793,219) and a modification thereof wherein a small amount of alkali is added thereto (Japanese Patent Examined Publication No. 37-11963).

As for attempts to produce branched chain fatty acids as the main product, U.S. Pat. No. 4,371,469 discloses a method using a Lewis acid or acid clay mineral such as montmorillonite in the presence of a mineral acid and a volatile hydrocarbon as promoters. However, this method is unsatisfactory as to branched chain fatty acid yield, which is about 30 to 60%. Another drawback is that the use of a mineral acid necessitates complicated production equipment for corrosion resistance and safety. There is a need for improvement in these aspects.

On the other hand, there have been some studies on the use of zeolite as a catalyst for various purposes based on its solid acid function, molecular sieve function, ion exchange function and ion adsorption function. For example, use of zeolite for skeletal isomerization of n-olefin and n-paraffin are known. Specifically, Japanese Patent Laid-Open Nos. 1-228923 and 1-159061 (U.S. Pat. No. 4,943,546) disclose skeletal isomerization of short-chain olefin and paraffin having 4 to 7 carbon atoms. Japanese Patent Laid-Open No. 5-246901 (EP Patent No. 523838) discloses skeletal isomerization of olefin of a short chain length of 4 to 10 carbon atoms. However, there is no report on the skeletal isomerization of long-chain olefin.

SUMMARY OF THE INVENTION

Accordingly, an object of the present invention is to provide a process for the preparation of long-chain fatty acids having branched alkyl chains, or alkyl esters thereof at a high selectivity in a high yield without using complicated equipment required when mineral acids or the like are used.

The present inventors have tackled the above object and found that the object can be accomplished by a process wherein unsaturated fatty acids having a total carbon number of 10 to 25 or alkyl esters thereof are subjected to reaction at 150° to 350° C. in the presence of water or a lower alcohol using a particular sort of zeolite as a catalyst for skeletal isomerization while suppressing formation of dimers.

In brief, the present invention is concerned with (1) A process for preparing branched chain fatty acids or alkyl esters thereof comprising at least a step wherein unsaturated fatty acids having 10 to 25 carbon atoms, alkyl esters thereof or mixtures thereof are subjected to skeletal isomerization reaction in the presence of water or a lower alcohol at a temperature of 150° to 350° C. using a zeolite as a catalyst, the zeolite having a linear pore structure of pore size that is small enough to retard dimerization and large enough to allow diffusion of the branched chain fatty acids or alkyl esters thereof; and (2) The process as described in (1) above further comprising a step wherein branched unsaturated fatty acids or alkyl esters thereof obtained by the skeletal isomerization reaction are hydrogenated to yield branched saturated fatty acids or alkyl esters thereof.

According to the process of the present invention for the preparation of branched chain fatty acids or esters thereof, long-chain fatty acids having branched alkyl chains or alkyl esters thereof can be produced in a high yield and at a high selectivity, without using complicated equipment required when mineral acids are used.

DETAILED DESCRIPTION OF THE INVENTION

The process of the present invention is to prepare branched chain fatty acids or alkyl esters thereof from unsaturated fatty acids having a total carbon number of 10 to 25 or alkyl esters or mixtures thereof, comprising at least a step wherein skeletal isomerization is carried out at 150° to 350° C. in the presence of water or a lower alcohol, using a zeolite catalyst having a linear pore structure with a pore size small enough to retard dimerization and large enough to allow diffusion of branched chain fatty acids or alkyl esters thereof.

When a starting material mixture contains both unsaturated fatty acids and alkyl esters thereof, both branched chain fatty acids and alkyl esters thereof can be produced, because both can be isomerized simultaneously. Such cases are also included in the technical scope of the present invention.

The unsaturated fatty acid used as the starting material is a fatty acid having unsaturated bonds and a total carbon number of 10 to 25, preferably 16 to 22. Considering industrial applications, it is further preferable that the major component of the starting material has a total carbon number of 18. Unsaturated fatty acids having a total carbon number of this rage are useful as starting materials for the synthesis of cosmetic bases, fiber treating agents, lubricating oil additives, etc.

With respect to the degree of unsaturation, i.e., the number of unsaturated carbon-carbon bonds, any unsaturated fatty acids may be used as long as one or more such bonds are present in a molecule. Specifically, the number of unsaturated bonds is normally 1 to 3, preferably 1. Therefore octadecenoic acid is the most preferable. The presence of an unsaturated bond in the molecule causes the formation of a cation as an intermediate, thereby facilitating the skeletal isomerization reaction. If a saturated fatty acid is used in large quantities as a starting material, formation of this intermediate cation is hampered, thereby making it difficult for isomerization to proceed.

Unsaturated fatty acids include oleic acid, palmitoleic acid, erucic acid, elaidic acid, linolic acid, linolenic acid and undecenoic acid, which can be derived from beef tallow, palm oil, safflower oil, tall oil, rapeseed oil, soybean oil, or the like. The mixture used as the starting material is a mixture containing two or more of these unsaturated fatty acids, or a mixture containing one or more of these unsaturated fatty acids and one or more of saturated fatty acids, various esters, and the like. In the case of a mixture, the content of the above-mentioned unsaturated fatty acids is normally not less than 40% by weight, preferably not less than 80% by weight in view of reaction rate and yield.

From the viewpoint of reaction selectivity, it is preferable that the above-described starting material contains 40 to 100% by weight of octadecenoic acids, such as oleic acid and elaidic acid.

Alkyl esters of unsaturated fatty acids having a total carbon number of 10 to 25 used as a starting material are those corresponding to the above-described unsaturated fatty acids. That is, alkyl esters of the unsaturated fatty acids exemplified above are used. Although the alkyl moiety is not subject to limitation as to carbon number, its carbon number is normally 1 to 3, preferably 1. Specific examples of alkyl esters include methyl esters, ethyl esters and propyl esters of the above-mentioned unsaturated fatty acids, with preference given to methyl esters.

When a mixture is used as the starting material, a mixture that contains at least one alkyl ester of the above-described fatty acids is used. Specifically, it is a mixture of one or more alkyl esters of these unsaturated fatty acids, or a mixture containing at least one alkyl ester of these unsaturated fatty acids and saturated fatty acids, various esters, etc. In the case of a mixture, the content of alkyl esters of the above-mentioned unsaturated fatty acids is normally not less than 40% by weight, preferably not less than 80% by weight in view of reaction rate and yield.

From the viewpoint of reaction selectivity, it is preferable that the above-described starting material be alkyl esters of unsaturated fatty acids containing 40 to 100% by weight of alkyl esters of octadecenoic acid, such as methyl oleate and methyl elaidate, or a mixture thereof.

Zeolite used for the present invention has a linear pore structure of pore size which is small enough to retard dimerization and large enough to allow diffusion of branched chain fatty acids or alkyl esters thereof. Significant by-product formation due to dimerization is undesirable, because it results in decreased yield of branched chain fatty acids, etc. On the other hand, insufficient diffusion of branched chain fatty acids, etc. is undesirable, because it results in decreased apparent catalyst activity. To meet the above requirements, the mean pore size of zeolite is normally about 4 to 9 Å, preferably about 5 to 8 Å, and more preferably about 6 to 7 Å, varying depending on the total carbon number of branched chain fatty acids, etc.

The term "linear pore structure" as used herein is a structure wherein pores are formed by at least linear continuous pathways.

In the present invention, any zeolite can be used, as long as it meets the above requirements. However, pentacyl type zeolite and mordenite type zeolite are preferred from the viewpoint of pore size, heat resistance, acid resistance and acid properties. The former is available only as a synthetic substance; the latter is available both as a natural substance and as a synthetic substance. The term "pentacyl type zeolite" as used herein, also referred to as ZSM-5 type, is a zeolite composed of oxygen 10-membered ring wherein zigzag pore pathways intersect tunnel-like pore pathways at right angles to form pores. The mordenite type zeolite, the highest in silicon content among naturally-occurring zeolites, is a zeolite composed of oxygen 12-membered ring wherein the pores are formed mainly by tunnel-like pore pathways [Shokubai Koza, Vol. 10, edited by the Catalysis Society of Japan, Kodansha Ltd. (1986)]. Although these zeolites can be synthesized by hydrothermal synthesis [J.C.S., 2158 (1948)], they are also commercially available. For example, commercial products of the pentacyl type include Ex504, Ex716, Ex717 and Ex1381, all being produced by Nissan Girdler Catalyst Co., Ltd. Commercial products of the mordenite type include the HSZ-600 series products, such as HSZ-620HOA, HSZ-640HOA and HSZ-690HOA, all being produced by Tosoh Corporation, and Zeolite Catalyst of Degussa Company.

Although it is preferable from the viewpoint of catalyst activity that the cation in zeolite be a proton, a zeolite of the sodium type, or the like, may be used in the reaction after being converted into the proton type by ion exchange. The silica/alumina molar ratio of zeolite is preferably 3 to 300, more preferably 5 to 200. The ratio is preferably not less than 3 in view of catalytic activity, and not more than 300 in view of yield. The "silica/alumina ratio (molar)" can easily be determined by atomic absorption photometry. Zeolite may be used in the reaction after a pretreatment by drying or burning.

In the present invention employing the above-described zeolite, the reaction is carried out in the presence of water or a lower alcohol. This is to suppress acid anhydride formation due to dehydration or dealcoholation of the starting material. This suppression is attributable to acid point modification of zeolite, such as conversion of Lewis acid point into Broensted acid point. It is preferable to add water when the starting material is unsaturated fatty acids; and an alcohol when the starting material is esters of unsaturated fatty acids.

The lower alcohol used is exemplified by alcohols having 1 to 3 carbon atoms. Specifically, methanol, ethanol, propanol, etc. are preferred, with a greater preference given to those having the same alkyl group as that of the starting fatty acid esters to be isomerized.

The isomerization reaction step in the present invention is carried out using the above-described starting material, zeolite, etc. As for specific reaction conditions, it is preferable that the reaction be carried out at 150° to 350° C. in the presence of 0.1 to 30 parts by weight of zeolite and 0.5 to 5 parts by weight of water or a lower alcohol, based on 100 parts by weight of the above-described unsaturated fatty acids and/or alkyl esters thereof. More preferably, the reaction is carried out at 200° to 290° C. in the presence of 1 to 20 parts by weight of zeolite and 1 to 3 parts by weight of water or a lower alcohol, based on 100 parts by weight of the above-described unsaturated fatty acids and/or alkyl esters thereof.

Also, the reaction may be carried out in a closed system where the reaction pressure is normally 2 to 50 kgf/cm². This is to prevent vaporization of water, alcohols and other low boiling substances in the system including those substances contained in a catalyst.

Since the catalyst tends to be poisoned by coke, the reaction normally takes 1 to 10 hours. If this problem is overcome, the reaction time can be shortened to several minutes or even several seconds. Also, continuous reaction becomes possible. Excessively long reaction time tends to cause thermal decomposition, resulting in decreased yield.

The reaction apparatus used is preferably an autoclave, because a pressurized reaction system is preferred. Although the atmosphere in the autoclave is preferably replaced with nitrogen or hydrogen, it may remain to be the air.

The product obtained by the above-described isomerization reaction contains branched chain unsaturated fatty acids or esters thereof, when the starting material is an ester of an unsaturated fatty acids, in a high yield. The product further contains polymeric fatty acids, such as dimer acids (polymeric fatty acid esters, when the starting material is esters of unsaturated fatty acids). The branched chain fatty acids, etc. thus obtained normally have alkyl side chains of 1 to 4 carbon atoms. They are obtained as a mixture of many isomers with different branching positions.

Furthermore, in the present invention, branched chain saturated fatty acids (esters of branched chain saturated fatty acids, when the starting material is esters of unsaturated fatty acids) can be obtained as follows. Namely, removal of catalyst zeolite and polymeric materials by filtration or distillation, the residue is hydrogenated in an autoclave by a known method, such as the method using a hydrogenation catalyst, (e.g., nickel or palladium/carbon), to yield a mixture of crude branched chain saturated fatty acids (esters of branched chain fatty acids, when the starting material is esters of unsaturated fatty acids). Then the crude product is purified by removing linear chain components by a known method, such as the compression method, the Emerson method and the Henkel method [U.S. Pat. No. 2,293,674, U.S. Pat. No. 2,421,157 and U.S. Pat. No. 2,800,493; J. Am. Oil Chem. Soc., 45, 471 (1968)], to yield branched chain saturated fatty acids (esters of branched chain saturated fatty acids, when the starting material is esters of unsaturated fatty acids) of high purity.

The order of filtration, distillation, hydrogenation (hardening), fractionation, etc. may be changed.

EXAMPLES

The present invention is hereinafter described in more details by means of the following working examples, but the present invention is not limited by them.

Example 1

Four hundred grams of oleic acid (SO-90L, produced by Kao Corporation; composition: 1% palmitic acid, 3% linolic acid, 89% octadecenoic acid, 2% hexadecenoic acid, 1% stearic acid), 32 g of H-mordenite type zeolite (HSZ-620HOA, produced by Tosoh Corporation; $SiO_2/Al_2O_3$ (molar ratio)=15; mean pore size, 6.7 to 7 Å) and 8 g of water were placed in an autoclave. After the inside atmosphere of the autoclave was replaced with nitrogen, the mixture was stirred. The inside of the autoclave was heated to 280° C. and kept in a steam atmosphere of 18 kgf/cm² for 6 hours. After cooling, the reaction mixture obtained was taken out from the autoclave, and the zeolite was filtered off. The filtrate was distilled under reduced pressure to yield 347.6 g of monomeric acids (branched chain unsaturated fatty acids).

The monomeric acids thus obtained and 3.5 g of 5% Pd/C were placed in an autoclave, and heated at 150° C. for 3 hours in a hydrogen atmosphere of 20 kgf/cm² until the reaction was complete. Then, the reaction mixture was cooled, and the catalyst was filtered off. The thus-obtained crude branched chain fatty acids were subjected to a conventional solvent fractionation procedure. Specifically, to the crude branched chain fatty acids, about 2-fold amount by weight of hexane was added. After this mixture was cooled to −15° C., the resulting crystal was filtered off. Then, the hexane was distilled off from the filtrate to yield 276.7 g of purified isostearic acid. The acid value (AV), saponification value (SV) and iodine value (IV) of the obtained product, as determined by JIS K3331, were as follows:

AV=162.7, SV=177.7, IV=9.1

The yield of monomeric acids and the yield and solidifying point of isostearic acid are shown in Table 1. Solidifying points were also determined in accordance with JIS K3331 (the same applies to the subsequent Examples).

As is evident from Table 1, according to the process of the present invention, monomeric acids can be obtained in a high yield in isomerization reaction. The final product (isostearic acid containing isomerized stearic acids) with a low solidifying point can also be obtained in a high yield.

Example 2

Four hundred grams of oleic acid (SO-90L, produced by Kao Corporation), 32 g of H-mordenite type zeolite (HSZ-620HOA, produced by Tosoh Corporation; $SiO_2/Al_2O_3$ (molar ratio)=19; mean pore size, 6.7 to 7 Å) and 8 g of water were placed in an autoclave. After the inside atmosphere of the autoclave was replaced with nitrogen, the mixture was stirred. The inside of the autoclave was heated to 280° C. and kept in a steam atmosphere of 18 kgf/cm² for 6 hours. After cooling, the reaction mixture obtained was taken out from the autoclave, and the zeolite was filtered off. The filtrate was distilled under reduced pressure to yield 338.8 g of monomeric acids.

The monomeric acids thus obtained and 3.5 g of 5% Pd/C were placed in an autoclave, and heated at 150° C. for 3 hours in a hydrogen atmosphere of 20 kgf/cm² until the reaction was complete. Then, the reaction mixture was cooled, and the catalyst was filtered off. The thus-obtained crude branched chain fatty acids were subjected to a conventional solvent fractionation procedure to yield 241.2 g of purified isostearic acid. The acid value (AV), saponification value (SV) and iodine value (IV) of the obtained product were as follows:

AV=167.0, SV=183.2, IV=4.4

Example 3

Four hundred grams of oleic acid (SO-90L, produced by Kao Corporation), 32 g of H-mordenite type zeolite (HSZ-640HOA, produced by Tosoh Corporation) and 4 g of water were placed in an autoclave. After the inside atmosphere of the autoclave was replaced with nitrogen, the mixture was stirred. The inside of the autoclave was heated to 300° C. and kept in a steam atmosphere of 16 kgf/cm² for 6 hours.

After cooling, the reaction mixture obtained was taken out from the autoclave, and the zeolite was filtered off. The filtrate was distilled under reduced pressure to yield 352.0 g of monomeric acids.

The monomeric acids thus obtained and 3.5 g of 5% Pd/C were placed in an autoclave, and heated at 200° C. for 3 hours in a hydrogen atmosphere of 20 kgf/cm² until the reaction was complete. Then, the reaction mixture was cooled, and the catalyst was filtered off. The thus-obtained crude branched chain fatty acids were subjected to a conventional solvent fractionation procedure to yield 228.2 g of purified isostearic acid. The acid value (AV), saponification value (SV) and iodine value (IV) of the obtained product were as follows:

AV=163.5, SV=179.1, IV=5.0

Incidentally, when isomerization is carried out at a relatively higher temperature as employed in Example 3, decomposition of oleic acid tends to occur. Therefore, it is recommended to isomerize oleic acid at a lower temperature.

Example 4

Four hundred Grams of oleic acid (SO-90L, produced by Kao Corporation), 32 g of H-mordenite type zeolite (HSZ-640HOA, produced by Tosoh Corporation) and 8 g of water were placed in an autoclave. After the inside atmosphere of the autoclave was replaced with hydrogen, the mixture was stirred. The inside of the autoclave was heated to 280° C. and kept in a steam atmosphere of 18 kgf/cm² for 6 hours. After cooling, the reaction mixture obtained was taken out from the autoclave, and the zeolite was filtered off. The filtrate was distilled under reduced pressure to yield 339.6 g of monomeric acids.

The monomeric acids thus obtained and 3.5 g of 5% Pd/C were placed in an autoclave, and heated at 150° C. for 3 hours in a hydrogen atmosphere of 20 kgf/cm² until the reaction was complete. Then, the reaction mixture was cooled, and the catalyst was filtered off. The thus-obtained crude branched chain fatty acids were subjected to a conventional solvent fractionation procedure to yield 282.9 g of purified isostearic acid. The acid value (AV), saponification value (SV) and iodine value (IV) of the obtained product were as follows:

AV=164.3, SV=181.5, IV=3.9

Example 5

Four hundred grams of oleic acid (SO-90L, produced by Kao Corporation), 16 g of H-mordenite type zeolite (HSZ-690HOA, produced by Tosoh Corporation; $SiO_2/AlO_3$ (molar ratio)=203; mean pore size 6.7 to 7 Å) and 8 g of water were placed in an autoclave. After the inside atmosphere of the autoclave was replaced with nitrogen, the mixture was stirred. The inside of the autoclave was heated to 280° C. and kept in a steam atmosphere of 18 kgf/cm² for 6 hours. After cooling, the reaction mixture obtained was taken out from the autoclave, and the zeolite was filtered off. The filtrate was distilled under reduced pressure to yield 342.7 g of monomeric acids.

The monomeric acids thus obtained and 3.5 g of 5% Pd/C were placed in an autoclave, and heated at 150° C. for 3 hours in a hydrogen atmosphere of 20 kgf/cm² until the reaction was complete. Then, the reaction mixture was cooled, and the catalyst was filtered off. The thus-obtained crude branched chain fatty acids were subjected to a conventional solvent fractionation procedure to yield 225.0 g of purified isostearic acid. The acid value (AV), saponification value (SV) and iodine value (IV) of the obtained product were as follows:

AV=159.9, SV=180.0, IV=4.3

Example 6

Four hundred grams of oleic acid (SO-90L, produced by Kao Corporation), 16 g of pentacyl type zeolite (EX1381 produced by Nissan Girdler Catalyst; $SiO_2/Al_2O_3$ (molar ratio)=14; mean pore size, 6 Å) and 8 g of water were placed in an autoclave. After the inside atmosphere of the autoclave was replaced with nitrogen, the mixture was stirred. The inside of the autoclave was heated to 280° C. and kept in a steam atmosphere of 18 kgf/cm² for 6 hours. After cooling, the reaction mixture obtained was taken out from the autoclave, and the zeolite was filtered off. The filtrate was distilled under reduced pressure to yield 336.1 g of monomeric acids.

The monomeric acids thus obtained and 3.5 g of 5% Pd/C were placed in an autoclave, and heated at 150° C. for 3 hours in a hydrogen atmosphere of 20 kgf/cm² until the reaction was complete. Then, the reaction mixture was cooled, and the catalyst was filtered off. The thus-obtained crude branched chain fatty acids were subjected to a conventional solvent fractionation procedure to yield 246.8 g of purified isostearic acid. The acid value (AV), saponification value (SV) and iodine value (IV) of the obtained product were as follows:

AV=171.1, SV=185.6, IV=5.1

Example 7

Six hundred grams of oleic acid (SO-90L, produced by Kao Corporation), 30 g of methanol, and 0.6 g of concentrated sulfuric acid were placed in a 4-neck flask, and heated to 100 ° C. Then, methanol was continuously blown into the flask for 7 hours until the reaction was complete. Then, the sulfuric acid catalyst was neutralized with sodium hydroxide. Then the reaction mixture was subjected to filtration and distillation to yield methyl oleate (AV=0.05, SV=191.6, IV=87.0).

Four hundred grams of the methyl oleate thus obtained, 16 g of mordenite type zeolite (HSZ-620HOA produced by Tosoh Corporation), and 8 g of methanol were placed in an autoclave. After the inside atmosphere of the autoclave was replaced with nitrogen, the mixture was stirred. The inside of the autoclave was heated to 280° C. and kept in a steam atmosphere of 18 kgf/cm² for 6 hours. After cooling, the reaction mixture obtained was taken out from the autoclave, and the zeolite was filtered off. The filtrate was distilled under reduced pressure to yield 332.0 g of a monomeric acid methyl esters (branched unsaturated fatty acid esters).

The monomeric acid methyl esters thus obtained and 2.8 g of 5% Pd/C were placed in an autoclave, and heated at 150° C. for 3 hours in a hydrogen atmosphere of 20 kgf/cm² until the reaction was complete. Then, the reaction mixture was cooled, and the catalyst was filtered off. The thus-obtained crude branched chain fatty acid methyl esters were subjected to a conventional solvent fractionation procedure to yield 250.8 g of purified methyl isostearate. The acid value (AV), saponification value (SV) and iodine value (IV) of the obtained product were as follows:

AV=0.11, SV=177.7, IV=3.5

Example 8

Four hundred grams of oleic acid (SO-90L, produced by Kao Corporation), 32 g of H-mordenite type zeolite (HSZ-640HOA produced by Tosoh Corporation) and 4 g of water were placed in an autoclave. After the inside atmosphere of the autoclave was replaced with nitrogen, the mixture was stirred. The inside of the autoclave was heated to 300° C. and kept in a steam atmosphere of 16 kgf/cm$^2$ for 6 hours. After cooling, the reaction mixture obtained was taken out from the autoclave, and the zeolite was filtered off.

380.5 g of the filtrate obtained, and 3.5 g of 5% Pd/C were placed in an autoclave, and heated at 200° C. for 3 hours in a hydrogen atmosphere of 20 kgf/cm$^2$ until the reaction was complete. Then, the reaction mixture was cooled, and the catalyst was filtered off. The filtrate was distilled under a reduced pressure to yield 323.4 g of hardened monomeric acids.

The hardened monomeric acids thus-obtained were subjected to a conventional solvent fractionation procedure to yield 263.2 g of purified isostearic acid. The acid value (AV), saponification value (SV) and iodine value (IV) of the obtained product were as follows:

AV=163.5, SV=179.1, IV=5.0

Example 9

Four hundred grams of 10-undecenoic acid (produced by Tokyo Kasei), 32 g of H-mordenite type zeolite (HSZ-640HOA produced by Tosoh Corporation) and 4 g of water were placed in an autoclave. After the inside atmosphere of the autoclave was replaced with nitrogen, the mixture was stirred. The inside of the autoclave was heated to 280° C. and kept in a steam atmosphere of 18 kgf/cm$^2$ for 6 hours. After cooling, the reaction mixture obtained was taken out from the autoclave, and the zeolite was filtered off.

390.5 g of the filtrate obtained and 3.7 g of 5% Pd/C were placed in an autoclave, and heated at 200° C. for 3 hours in a hydrogen atmosphere of 20 kgf/cm$^2$ until the reaction was complete. Then, the reaction mixture was cooled, and the catalyst was filtered off. The filtrate was distilled under a reduced pressure to yield 250.3 g of hardened monomeric acids.

The hardened monomeric acids thus-obtained were subjected to a conventional solvent fractionation procedure to yield 233.2 g of purified isostearic acid. The acid value (AV), saponification value (SV) and iodine value (IV) of the obtained product were as follows:

AV=250.3, SV=300.2, IV=5.0

Comparative Example 1

Four hundred grams of oleic acid (SO-90L, produced by Kao Corporation), 16 g of montmorillonite (KSF, mean inter-layer distance of 4 Å, produced by Nissan Girdler Catalyst Co., Ltd.) and 8 g of water were placed in an autoclave. After the inside atmosphere of the autoclave was replaced with nitrogen, the mixture was stirred. The inside of the autoclave was heated to 240° C. and kept in a steam atmosphere of 13 kgf/cm$^2$ for 6 hours. After cooling, the reaction mixture obtained was taken out from the autoclave, and the montmorillonite was filtered off. The filtrate was distilled under a reduced pressure to yield 206.8 g of monomeric acids.

The monomeric acids thus obtained and 3.5 g of 5% Pd/C were placed in an autoclave, and heated at 150° C. for 3 hours in a hydrogen atmosphere of 20 kgf/cm$^2$ until the reaction was completed. Then, the reaction mixture was cooled, and the catalyst was filtered off. The crude branched fatty acids thus obtained were subjected to a conventional solvent fractionation procedure to yield 124.1 g of purified isostearic acid. The acid value (AV), saponification value (SV) and iodine value (IV) of the obtained product were as follows:

AV=162.7, SV=185.1, IV=7.2

Comparative Example 2

Four hundred grams of oleic acid (SO-90L, produced by Kao Corporation), 16 g of activated clay (CS-1, mean inter-layer distance of 4 Å, produced by Mizusawa Kagaku) and 8 g of water were placed in an autoclave. After the inside atmosphere of the autoclave was replaced with nitrogen, the mixture was stirred. The inside of the autoclave was heated to 240° C. and kept in a steam atmosphere of 14 kgf/cm$^2$ for 6 hours. After cooling, the reaction mixture obtained was taken out from the autoclave, and the semisynthetic clay was filtered off. The filtrate was distilled under a reduced pressure to yield 167.6 g of monomeric acids.

The monomeric acids thus obtained and 3.5 g of 5% Pd/C were placed in an autoclave, and heated at 150° C. for 3 hours in a hydrogen atmosphere of 20 kgf/cm$^2$ until the reaction was complete. Then, the reaction mixture was cooled, and the catalyst was filtered off. The crude branched fatty acids thus obtained were subjected to a conventional solvent fractionation procedure to yield 98.4 g of purified isostearic acid. The acid value (AV), saponification value (SV) and iodine value (IV) of the obtained product were as follows:

AV=165.5, SV=186.2, IV=7.7

Comparative Example 3

Four hundred grams of oleic acid (SO-90L, produced by Kao Corporation), 32 g of USY type zeolite (HSZ-330HUA, mean pore size of 4 Å, produced by Tosoh Corporation) and 8 g of water were placed in an autoclave. After the inside atmosphere of the autoclave was replaced with nitrogen, the mixture was stirred. The inside of the autoclave was heated to 240° C. and kept in a steam atmosphere of 12 kgf/cm$^2$ for 6 hours. After cooling, the reaction mixture obtained was taken out from the autoclave, and the zeolite was filtered off. The filtrate was distilled under a reduced pressure to yield 328.4 g of monomeric acids.

The monomeric acids thus obtained and 3.5 g of 5% Pd/C were placed in an autoclave, and heated at 150° C. for 3 hours in a hydrogen atmosphere of 20 kgf/cm$^2$. After completion of the reaction, the reaction mixture was cooled, and the catalyst was filtered off. The crude branched fatty acids thus obtained were subjected to a conventional solvent fractionation procedure to yield 50.8 g of purified isostearic acid. The acid value (AV), saponification value (SV) and iodine value (IV) of the obtained product were as follows:

AV=167.2, SV=181.5, IV=5.3

An atomic absorption spectrometry of the isomerization product revealed that aluminum was eluted because the USY type zeolite underwent structural destruction during isomerization reaction. The low reaction rate due to destruction of the catalyst explains the significantly low yield of isostearic acids.

Comparative Example 4

Sixteen grams of mordenite type zeolite (HSZ-620HOA, produced by Tosoh Corporation) was baked at 600 ° C. for 2 hours. The baked zeolite and 400 g of oleic acid (SO-90L, produced by Kao Corporation) were place in an autoclave.

After the inside atmosphere of the autoclave was replaced with nitrogen, the mixture was stirred. The inside of the autoclave was heated to 240° C. and kept in a steam atmosphere of 3 kgf/cm² for 6 hours. After cooling, the reaction mixture obtained was taken out from the autoclave, and the zeolite was filtered off. The filtrate was distilled under a reduced pressure to yield 336.0 g of monomeric acids.

However, almost all of the monomeric acids thus obtained were octadecenoic acids including oleic acid and elaidic acid. When dried zeolite is used without adding water as in Comparative Example 4, skeletal isomerization hardly proceeds.

Comparative Example 5

Four hundred Grams of oleic acid (SO-90L, produced by Kao Corporation), 16 g of H-mordenite type zeolite (HSZ-620HOA; $SiO_2/AL_2O_3$ (molar ratio)=15; mean pore size of 6.7 to 7 Å, produced by Tosoh Corporation) and 8 g of water were placed in an autoclave. After the inside atmosphere of the autoclave was replaced with nitrogen, the mixture was stirred. The inside of the autoclave was heated to 130° C. and kept in a steam atmosphere of 3 kgf/cm² for 6 hours. After cooling, the reaction mixture obtained was taken out from the autoclave, and the zeolite was filtered off. The filtrate was distilled under a reduced pressure to yield 360.1 g of monomeric acids.

However, almost all of the monomeric acids thus obtained were octadecenoic acids including oleic acid and elaidic acid. When the reaction temperature is low as in Comparative Example 5, skeletal isomerization hardly proceeds.

Table 1 shows the yields of monomeric acids and monomeric acid methyl esters; the yields of isostearic acid and isostearic acid methyl ester respectively based on the contents of linear unsaturated fatty acids or esters thereof in the starting materials; and solidifying points of isostearic acid and isostearic acid methyl ester in Examples and Comparative Examples.

TABLE 1

|  | Yield of Monomeric Acids (wt %) | Yield of Isostearic Acids (wt %) | Solidifying Point (titre:°C.) |
|---|---|---|---|
| Ex.1 | 86.9 | 69.2 | −3.5 |
| Ex.2 | 84.7 | 60.3 | −2.1 |
| Ex.3 | 88.0 | 57.1 | −3.7 |
| Ex.4 | 84.9 | 70.7 | −2.9 |
| Ex.5 | 87.3 | 56.3 | −3.0 |
| Ex.6 | 84.0 | 61.7 | −3.6 |
| Ex.7 | 82.3* | 59.5* | (Not determined) |
| Ex.8 | 85.0** | 65.8 | −3.9 |
| Ex.9 | 62.6 | 58.3 | (Not determined) |
| Comparative Ex.1 | 51.7 | 31.0 | 5.3 |
| Comparative Ex.2 | 41.9 | 24.6 | 4.8 |
| Comparative Ex.3 | 82.1 | 20.5 | 2.9 |
| Comparative Ex.4 | 86.0 | (Not separated) | (Not determined) |
| Comparative Ex.5 | 90.0 | (Not separated) | (Not determined) |

*Yield of methyl esters
**Yield of hardened monomeric acids

As shown in Table 1, like in Example 1, the yields of monomeric acids or monomeric acid methyl esters, and the yields of the final products (isostearic acid or isostearic acid ester) were high in Examples 2 to 9. Also, the solidifying points of the final products were low in Examples 2 to 9. On the contrary, in Comparative Examples 1 to 3, the yields of monomeric acids or monomeric acid esters and the yields of isostearic acid or isostearic acid ester were low. Also, the solidifying points of the final products were higher than those in Examples.

In Table 2, solidifying points of commercially available isostearic acid products are listed (titre: °C., JIS K3331).

As shown in Table 2, the isostearic acids obtained by the process of the present invention show higher solidifying points as compared with commercially available isostearic acid products.

TABLE 2

| Manufacturer | Product Name | Solidifying Point (°C.) |
|---|---|---|
| Henkel Corporation | Emersol 871 | 6.9 |
| Henkel Corporation | Emersol 875 | 8.6 |
| Unichema Chemie B.V. | PRISORINE ISAC3505 | 4.4 |
| Union Camp Corporation | Century 1105 | 3.3 |

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for preparing branched chain fatty acids or alkyl esters thereof comprising the steps of subjecting unsaturated fatty acids having 10 to 25 carbon atoms, alkyl esters thereof or mixtures thereof to a skeletal isomerization reaction in the presence of water or a lower alcohol at a temperature of 150° to 350° C. using a zeolite as a catalyst, wherein said zeolite has a linear pore structure of pore size that is small enough to retard dimerization and large enough to allow diffusion of said branched chain fatty acids or alkyl esters thereof; and isolating branched chain fatty acids or alkyl esters thereof or mixtures thereof from the reaction mixture obtained by the skeletal isomerization reaction.

2. The process according to claim 1, wherein said zeolite is pentacyl zeolite or mordenite zeolite.

3. The process according to claim 1, wherein a mean pore size of said zeolite is in the range of from 4 to 9 Å.

4. The process according to claim 1, wherein a molar ratio of silica to alumina in said zeolite ($SiO_2/Al_2O_3$) is 3 to 300.

5. The process according to claim 1, wherein an amount of said zeolite used is 0.1 to 30 parts by weight, based on 100 parts by weight of the unsaturated fatty acids or alkyl esters thereof.

6. The process according to claim 1, wherein an amount of said water or said lower alcohol is 0.5 to 5 parts by weight, based on 100 parts by weight of the unsaturated fatty acids or alkyl esters thereof.

7. The process according to claim 1, wherein the skeletal isomerization reaction is carried out under a pressure of 2 to 50 kgf/cm².

8. The process according to claim 1, wherein a starting material contains 40 to 100% by weight of at least one of octadecenoic acids and alkyl esters thereof.

9. The process according to any one of claims 1 to 8, further comprising a step wherein branched unsaturated fatty acids or alkyl esters thereof obtained by the skeletal isomerization reaction are hydrogenated to yield branched saturated fatty acids or alkyl esters thereof.

10. The process according to claim 1, wherein said unsaturated fatty acids have 16 to 22 carbon atoms.

* * * * *